United States Patent [19]
Scott

[11] Patent Number: 5,962,528
[45] Date of Patent: Oct. 5, 1999

[54] PROSTAGLANDIN $E_2/F_{2\alpha}$ COMBINATION FOR TREATING IMPOTENCE

[76] Inventor: Nathan Earl Scott, 610 Laguna Rd., Fullerton, Calif. 92835

[21] Appl. No.: 09/038,378

[22] Filed: Mar. 11, 1998

Related U.S. Application Data

[63] Continuation-in-part of application No. 09/005,087, Jan. 9, 1998, abandoned, which is a continuation-in-part of application No. 08/090,483, Jul. 12, 1993, Pat. No. 5,708,031, which is a continuation of application No. 07/860,107, Mar. 30, 1992, abandoned, which is a continuation of application No. 07/725,350, Jul. 3, 1991, abandoned.

[51] Int. Cl.$^6$ .................................................. A61K 31/557
[52] U.S. Cl. ............................................................ 514/573
[58] Field of Search ............................................. 514/573

[56] References Cited

U.S. PATENT DOCUMENTS

| | | | |
|---|---|---|---|
| 4,311,707 | 1/1982 | Birnbaum et al. | 514/573 X |
| 4,801,587 | 1/1989 | Voss et al. | 514/248 |
| 4,955,878 | 9/1990 | See et al. | 514/573 X |
| 5,242,391 | 9/1993 | Place et al. . | |

FOREIGN PATENT DOCUMENTS

| | | |
|---|---|---|
| WO9002545 | 3/1990 | WIPO . |
| WO9116021 | 10/1991 | WIPO . |

OTHER PUBLICATIONS

Schramek et al, Derwent Drug File Abstracts, vol. 90, abstract No. 01345, 1989.
"Impotence," *Medical Aspects of Human Sexuality*, pp. 66–68, May 1991.
Gauger, Laura J. and Curet, Louis B., "Comparative Efficacy of Intravaginal Prostaglandin E–2 in the Gel and Suppository Forms for Cervical Ripening,"*DICP, The Annals of Pharmacotherapy,*25:456–460, May 91.
Cavallini, Giorgio, "Minoxidil vs. Nitroglycerine: A Perspective Double Blind Controlled Trial in Transcutaneous Erection Facilitation for Organic Impotence,"*The Journal of Urology*, 146:50–53. Jul. 1991.
Artoux, Michelle J., "Alprostadil in Impotence, "*DICP, The Annals of Pharmacotherapy*, 25:363–365, Apr. 1991.
Burnakis, Thomas G., "Amyl Nitrite for the Treatment of Penile Tumescence," *Hospital Pharmacy*, 26:343–344, Apr. 1991.
*Physicians' Desk Reference*, 45th ed., pp. 627–628, 1991.
Lehninger, Albert L., *Biochemistry*, 2nd ed., 1975.
Ganong, William F., *Review of Medical Physiology*, 7th ed., pp. 187, 226, 1975.
*Physicians' Desk Reference*, 45th ed., pp. 2250–2251, 1991.
Catanzarite, Valerian A. and Aisenbrey, Gary, "Prostaglandins: Mundane and Visionary Applications," *Contemporary Ob/Gyn*, pp. 21–41, Oct. 1987.
"Agents for Patent Ductus Arteriosus," *Facts & Comparisons*, pp. 732–732a, Nov. 1989.

"Prostin E–2," package insert of the Upjohn Company, revised Oct. 1990.
"Hemabat," package insert of the Upjohn Company, reivsed Nov. 1989.
Andersen et a., "Molecular Basis for Prostaglandin Potency, III. Tests of the Significance of the "Hairpin Conformation" in Biorecognition Phenomena,*Prostaglandins*," vol. 22, No. 5, pp. 841–855, Nov. 1981.
Bernard et al., "The Roles of Urologist and Patient in Autoinjection Therapy for Erectile Dysfunction," *Contemporary Urology*, pp. 21–26, Jan./Feb. 1990.
Dray et al., "Prostaglandins of the E Series Inhibit Release of Noradrenaline in Rat Hypothalamus by a Mechanism Unrelated to Classical $\alpha_2$, Adrenergic Presynaptic Inhibition," *Neuropharmacology*, vol. 23 No. 4, pp. 457–462, 1984.
Dunn, C.D.R., "Prostaglandins and Erythropoiesis: Structure/Action Relationships and Identification of the Prostaglandin Responsive Cells," *Blut*, 42, pp. 307–314, 1981.
Ganong, William F., "Chapter 17. Energy Balance, Metabolism and Nutrition," *Review of Medical Physiology*, pp. 229–231, 8th Edition, 1977.
Larock et al., "Organopalladium Approaches to Prostaglandins, Synthesis of $PGF_{2\alpha}$ by the Controlled, One–Step, Palladium–Promoted, Intermolecular Coupling of Three Different Alkenes," *J. Am. Chem. Soc.*, 113, 7815–7816, 1991.
Pasargiklian et al., Clinical, Functional and Pathogenetic Aspects of Bronchial Reactivity to Prostaglandins $F_{2\alpha}$, $E_1$, and $E_2$, *Advances in Prostaglandin and Thromboxane Research*, vol. 1, pp. 461–475, 1976.
Takahashi et al., "Glomerular Actions of a Free Radical-Generated Novel Prostaglandin, 8–epi–Prostaglandin $F_{2\alpha}$, in the Rat," *J. Clin. Invest.*, vol. 90, 136–141, Jul. 1992.
Windholz, et al., "Prostaglandin(s)", *The Merck Index*, pp. 1134–1135, 1983.
Wolfson et al., "Intraurethral Prostaglandin E–2 Cram: A Possible Alternative Treatment for Erectile Dysfunction", *Urology*, vol. 42, No. 1, Jul. 1993 and Abstract of Article.
Zoutendam et al., "Quantitative Determination of Alprostadil ($PGE_1$) in Bulk Drug and Pharmaceutical For ulations by High–Performance Liquid Chromatography," *Journal of Chromatography*, 283, 273–280, 1984.

*Primary Examiner*—William R. A. Jarvis
*Attorney, Agent, or Firm*—Michael J. Ram; Loeb & Loeb LLP

[57] ABSTRACT

Disclosed herein is method of treating and a composition for treating erectile dysfunction in a male patient by administering to the patient a unit dose of a formulation comprising an erectile dysfunction treating amount of a prostaglandin, namely prostaglandin $E_1$, prostaglandin $E_2$, or pharmaceutically acceptable salts or derivatives thereof, wherein the prostaglandin is formulated with a small amount of prostaglandin $F_{\alpha 2}$ together with a pharmaceutically acceptable delivery medium and/or a lubricant.

12 Claims, No Drawings

PROSTAGLANDIN $E_2/F_{2\alpha}$ COMBINATION FOR TREATING IMPOTENCE

This is a continuation-in-part of Ser. No. 09/005,087 filed Jan. 9, 1998 now abandoned which is a continuation-in-part of Ser. No. 08/090,483, filed Jul. 12, 1993, now U.S. Pat. No. 5,708,031, issued Jan. 13, 1998, which is a continuation of Ser. No. 07/860,107 filed Mar. 30, 1992, now abandoned, which is a continuation of Ser. No. 07/725,350 filed Jul. 3, 1991, now abandoned.

BACKGROUND OF THE INVENTION

The present invention relates to the treatment of impotence, and, more particularly, to the reversible pharmaceutical treatment of impotence using prostaglandin $PGE_2$.

In excess of about 10 million men in the United States alone exhibit sufficient erectile dysfunction that they can be characterized as effectively impotent. Impotence in the human male can arise from a variety of psychological and physiological etiologies. For example, long term diabetes, damage to the spinal cord, multiple sclerosis, or nerve damage resulting for example from lower abdomen or prostate surgery, and advancing age can result in impotence. For differing reasons, each of the foregoing result in an inability to pressurize the corpora cavernosa, which can result in turn from either an insufficient arterial inflow on the supple side, or an insufficient increase in the venous output resistance to blood flow.

A wide variety of mechanical means have been provided, in an effort to overcome erectile dysfunction. For example, U.S. Pat. No. 4,596,242 to Fischell discloses a surgically implantable hydraulic system, having a fluid reservoir and pressure generator, a patient manipulable valve, a pressure reservoir and a distensible member responsive to actuation of the valve. A variety of other prior art mechanical implants and other devices for this purpose are described in the Background of the Invention section of the U.S. Pat. No. 4,596,242.

In addition to the mechanical efforts to overcome erectile dysfunction, pharmaceutical approaches have been tried as well. For example, prostaglandin E1 has been observed to produce erection in some cases, but only by direct percutaneous injection into the penis.

Notwithstanding the foregoing, there remains a need for an improved treatment of erectile dysfunction. Surgical implantation and/or repeated injections range from disfavored to medically disadvantageous, and do not, as a whole, provide a satisfactory solution to the problem. From a patient usability standpoint, erectile dysfunction would most advantageously be treated on a self-administration basis, without the need of surgical intervention or repeated injections of a pharmaceutical agent. This problem has been addressed by the use of $PGE_2$ as claimed in my U.S. application Ser. No. 08/090,483. However, some patients on using urethral placement of $PGE_2$ materials have experienced urethral burning and aching within the genital area. Therefore, there is a need for a $PGE_2$ formulation which avoids these negative sensations but does not interfere with the effectiveness of the $PGE_2$ for treatment of impotence.

SUMMARY OF THE INVENTION

In accordance with one aspect of the present invention, there is provided method of treating erectile dysfunction in a male patient, comprising the step of administering to the patient a unit dose of a formulation comprising an erectile dysfunction treating amount of prostaglandin $E_2$ compound, or pharmaceutically acceptable salts or derivatives thereof. The prostaglandin $E_2$ compound is preferably formulate with a small amount of prostaglandin $F_{2\alpha}$ together with a pharmaceutically acceptable delivery medium and/or a lubricant.

A unit dose of the formulation in accordance with the present invention will typically be less than about 5 cc in volume, preferably less than about 3 cc and most preferably within the range of from about 1 cc to 2 cc. The amount of active ingredient in a unit dose will typically be within the range of from about 0.2 mg to about 5.0 mg. More preferably, the amount of prostaglandin $E_2$ in a unit dose will be within the range of from amount 0.6 mg to about 1.8 mg. It has now been found that adding prostaglandin $F_{2\alpha}$ in amounts of about 0.5 micrograms (0.5 µg) to about 5.0 µg to the prostaglandin $E_2$ prevents the burning and aching with noticeably interfering with effectiveness of the $PGE_2$. A preferred amount is 1.0 µg of $PGF_{2\alpha}$ per 1 mg of $PGE_2$.

The administration step of the method in accordance with the present invention comprises the transurethral administration of the unit dose of formulation. In an embodiment where the formulation comprises a cream, gel form or saline solution, the formulation is preferably transurethrally instilled or inserted such as by extrusion through syringe or unit dose administration packet comprising an elongate tubular administration tip.

In an embodiment of the present invention, wherein the administrable form of the formulation comprises a relatively rigid suppository, the suppository can be manually inserted into the distal opening of the urethra.

A further embodiment provides for urethral insertion of a removable wand, which may be porous, which carries the unit dose in a form which transfers over a controlled period of time through the urethral mucosa.

In accordance with a further aspect of the present invention, there has been provided a formulation and method for relieving the erectile dysfunction treating effects of the application of a formulation comprising prostaglandin $E_2$, or of treating priapism of other etiology. In accordance with this antidote method, an effective antidotal amount of a formulation comprising a 15 methyl substituted prostaglandin F2α or pharmaceutically acceptable salt is administered in the same manner as described above.

These and further objects and advantages of the present invention will become apparent from the Detailed Description of Preferred Embodiments which follows, considered together with the appended Claims.

DETAILED DESCRIPTION OF PREFERRED EMBODIMENTS

The prostaglandin are a series of cyclic derivatives of certain unsaturated fatty acids. They are found in a variety of tissues, including the prostate gland, the seminal vesicles, the lungs and the brain. These naturally occurring prostaglandin are derived by cyclization of 20-carbon unsaturated fatty acids such as arachidonic acid. See Lehninger, Albert L., Biochemistry, 2d ed. (1975), p. 300 (hereinafter "Lehninger").

Carbon atoms of the fatty acid backbone are cyclized to form a characteristic 5-membered ring. The prostaglandin are divided into a number of groups, including those designated A-F, based on the configuration of the ring structure. Prostaglandin also differ in stereochemistry and in the number of side chain double bonds which are conventionally indicated by a subscript number. Thus, for example, prostaglandin $E_2$ ("$PGE_2$") has the ring configuration characteristic of the E group and contains two side chain double bonds. The chemical name for PGE$_2$ is (5Z, 11α, 13E, 15S)-11, 15-Dihydroxy-9-oxo-prosta-5, 13-dien-1-oic acid and the structural formula of one form is represented in Formula I, below. The molecular formula is C$_{20}$H$_{32}$ O$_5$.

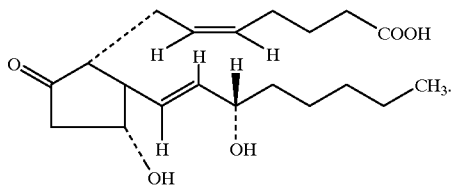

I

The biosynthesis of prostaglandin has been well characterized. See, eg., Lehninger at p. 687. In a typical biosynthetic pathway, exemplified by production of PGE$_2$, the essential fatty acid linoleic acid is converted into the 20-carbon arachidonic acid, which is then acted upon by prostaglandin synthase, doxygenase enzyme. Oxygen atoms are added at carbon atoms 9 and 15, and the product is cyclized by formation of a bond between carbon atoms 8 and 12. In the presence of reduced glutathione, this syslized product undergoes conversion into prostaglandin PGE$_2$. Other types of naturally occurring prostaglandins are derived from different polyunsaturated fatty acids.

In about the 1960's, prostaglandin were isolated from a particular species of Caribbean coral, which made them more widely available for research. Catanzarite, Valerian A. and Gary Aisenbrey, Contemporary OB/GYN (October 1987), p. 22 (hereinafter "Catanzarite"). A large number of natural and synthetic analogues of he prostaglandin are now known. Lehninger at 687.

The prostaglandin are known to produce often unpredictable effects over a very wide range of biological activities of a hormonal or regulatory nature. Prostaglandin have been reported to both lower and raise blood pressure, to inhibit gastric secretion, dilate bronchi, inhibit lipolysis, antagonize vasopressin-induced antidiarrhesis, constrict the pupil, increase and decrease the intraocular pressure and produce contraction of the uterus. See, e.g., Ganong, William F., Review of Medical Physiology, 7th ed. (1975), p. 226 (hereinafter "Ganong"). The naturally occurring prostaglandin all appear to be capable of affecting the control of vascular and other smooth muscle contractions. In the central nervous system, prostaglandin are known to modify responses to certain synaptic transmitters. They have been reported to mimic the actions of some hormones and to inhibit the actions of certain others. See Ganong at 226.

Two of the most extensively studied of the prostaglandin are PGE$_2$, and PGF$_{2\alpha}$. Both of these molecules are synthesized within the pregnant and non-pregnant uterus. While PGE$_2$ and PGF$_{2\alpha}$ are similar in mediating some effects, they are different with respect to certain others. Both cause uterine contractions, but they predominate at different sites within the uterus—PGE$_2$ in the lower uterine segment, PGF$_{2\alpha}$ is more important in generating uterine contractions. PGE$_2$ elevates body temperature, whereas PGF$_{2\alpha}$ has no apparent effect on body temperature. PGE$_2$ is a vasodilator and bronchodilator, while PGF$_{2\alpha}$ is a bronchoconstrictor and vasoconstrictor. (See Catanzarite at 21-22.)

Prostaglandin have been used in gynecology for pregnancy termination. Preparing the cervix with prostaglandin suppository has been found to reduce the incidence of cervical laceration and significant bleeding (Catanzarite at 22). Synthetic analogues of prostaglandin PGE$_2$, such as 16-16-dimethyl PGE$_2$ and 9-methylene PGE$_2$, have proven useful for the induction of first trimester abortions. Such procedures typically use vaginal suppositories containing 20 milligrams PGE$_2$ or 3 milligrams 15-methyl PGF$_{2\alpha}$, or by repeated intramyometrial injections of 15-methyl PGF$_{2\alpha}$, or by infusing a PGF$_{2\alpha}$-urea mixture (20 milligrams of PGF$_{2\alpha}$ and 40 milligrams of urea in 100 Ml of 5% dextrose in water) into the amniotic sac.

In obstetrics, prostaglandin have been used for cervical ripening, labor induction and control of post-partum hemorrhage. Catanzarite at 29. For cervical ripening, PGE$_2$ had been given intravenously, orally and vaginally, but the preferred route is intracervically. A PGE$_2$ gel is now commercially available in Scandinavia, and another PGE$_2$, gel is being investigated in the United States. The PGE$_2$ gel can also be used for labor induction (3–5 mg of PGE$_2$, prepared by blending a 20 mg suppository with 60 mL of lubricating jelly and using 9–15 mL of the mixture, is placed in the vagina) (Catanzarite at 32). Prostaglandin have also been utilized to control post-partum hemorrhage.

Since circulating prostaglandin can be rapidly metabolized in the lungs, liver and kidneys, a number of synthetically modified prostaglandin have been developed that are not metabolized as quickly (See, e.g., Catanzarite at 32).

Prostaglandin PGE$_2$, also known as the "Prostin E$_2$" brand of "dynoprostone," is available from Upjohn Company in the form of a vaginal suppository. Indications and usage reported by Upjohn are (i) termination of pregnancy from the 12th through the 20th gestational week, (ii) evacuation of the uterine contents in the management of missed abortion or intrauterine fetal death up to 28 weeks of gestational age, and (iii) in the management of non-metastic gestional trophoblastic disease (benign hydatidiform mole). See The Upjohn Co., Prostin E$_2$ product description 810 994 009, October, 1990.

Contraindications to the use of prostaglandin PGE$_2$ include hypersensitivity to dynoprostone, acute pelvic inflammatory disease, or patients with active cardiac pulmonary renal or hepatic disease. Upjohn notes that although carcinogenic bioassay studies have not been conducted in animals for PGE$_2$ (because of the limited indication for use and the short duration of administration), there was no evidence of mutagenicity in either the Micronucleus Test or in the Ames Assay. Upjohn also indicates that a number of adverse reactions may be observed with the use of PGE$_2$ for abortions. These adverse reactions are related to PGE$_2$'s contractile effect on smooth muscle and include vomiting, temperature elevations, diarrhea, nausea, transient diastolic blood pressure decreases, and a number of other effects. Upjohn's vaginal suppository contains 20 mg of PGE$_2$ in a mixture of glycerides of fatty acids.

Upjohn markets and (15S)-15-methyl analogue of prostaglandin PGF$_{2\alpha}$ under the brand name Hemabate®, and also known as "carboprost tromethamine sterile solution." The structural formula of Hemabate® is represented in:

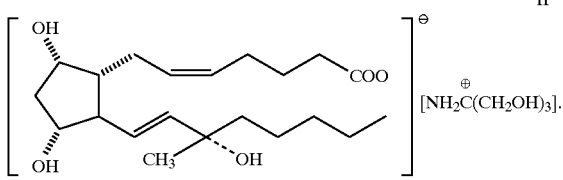

Upjohn reports that Hemabate® is indicated for aborting pregnancy between the 13th and 20th weeks of gestation, in certain condition related to second trimester abortions, and in the treatment of post-partum hemorrhage. See The Upjohn Co., product description 814 350 002, November, 1989. For abortion, the prostaglandin solution is injected using a syringe and administered deep in the muscle. Intramuscular injection is also used for treating post-partum uterine bleeding.

Upjohn also markets prostaglandin $PGE_1$, as the "Prostin VR Pediatric" brand of "alprostadil sterile solution," which is used to temporarily maintain the patency of the ductus arteriosus until corrective surgery can be performed in neonates having congenital heart defects and who depend upon the patent ductus for their survival. For the administration of $PGE_1$ in neonates, Upjohn recommends continuous intravenous infusion into a large vein, or administration through an umbilical artery catheter placed at the ductal opening. See The Upjohn Co., product description 811 987 004, in Physician's Desk Reference, 45th Edition, p.2250 (1991).

Quite surprisingly, the inventor herein has discovered that transurethral application of $PGE_2$ can in many cases provide an effective, reversible treatment of erectile dysfunction in human males. Thus, in accordance with one embodiment of the present invention, $PGE_2$ or a pharmaceutically acceptable salt, ester or other derivative thereof is formulated together with a carrier medium which may comprise any of a variety of additional excipients or adjuvants into a form suitable for transurethral delivery. In accordance with another aspect of the present invention, there is provided an antidote for reversing the effects of the foregoing $PGE_2$ treatment, comprising administration of an antidotal amount of $PGF_{2\alpha}$, or pharmaceutically acceptable salts, esters or derivatives thereof. Preferably, 15-methyl $PGF_{2\alpha}$ is utilized for this purpose.

Preferably, the $PGF_2$ or $PGF_{2\alpha}$ formulation will comprise a cream or gel, although a more solid form such as pellets or a rod-shaped suppository body may also be used. Although low viscosity gels or liquids may also be formulated, the liquid form may present handling and delivery difficulties and may not present a sufficient dwell time in the urethra to permit absorption of an efficacious amount of the active ingredient.

Administration of the cream or gel form may be accomplished by transurethral delivery using a syringe without a needle, or with a short blunt cannula attached. The gel or cram forms are preferably provided in unit dose amounts for self administration by the patient. For this purpose, compressible unit dose packages are preferably provided with an elongate tubular delivery spout, sized for transurethral insertion. Following transurethral installation of any of the liquid, gel or cream forms, the distal end of the urethra is preferably occluded, such as by manual pressure for up to several minutes, to permit sufficient dwell time for absorption.

While transurethral delivery of $PGE_2$ is a highly effective means of treating impotence, an undesirable side effect in some individuals is a sensation of urethral burning or pain in the genital area. One approach is to add a lubricant and/or a local anesthetic for desensitization thus masking these side effects. In one embodiment, the $PGE_2$, lubricant and anesthetic are all formulated into a convenient cream. This cream may be prepared, for example, by mixing one Upjohn Prostin E® $PGE_2$ suppository together with 10 cc of a lidocaine jelly such as Xylocaine® 2% jelly (available from Astra Pharmaceutical Products) and 50 cc. of a surgical lubricant such as K-Y jelly (available from Johnson & Johnson). Lidocaine HCl, available in a variety of formulations, comprises acetamide, 2-(diethylamino)-N-(2, 6-dimethylphenyl)-monohydrochloride.

The amount of lubricant and the amount and concentration of anesthetic can be varied considerably as will be apparent to one of skill in the art. For example, lidocaine jelly can be used having anywhere from about 1% to about 10% and preferably about 2% lidocaine. In general, the anesthetic level can largely be dictated by patient preference, as determined through routine experimentation. Although the incidence of adverse effects with Xylocaine® 2% jelly is very low, caution should be exercised when applying large amounts since the frequency of adverse effects is directly proportional to the total dosage of the local anaesthetic administered. See Astra Pharmaceuticals, product description 021838R11, June 1986; in Physician's Desk Reference, 45th Edition (1991), at p. 628.

A variety of other anesthetic agents can also be used with the formulation of the present invention, as will be appreciated by one of skill in the art. For example, novocaine, procaine, tetracaine or benzocaine may be selected. Patents allergic to para-aminobenzoic acid derivatives such as procaine, tetracaine and benzocaine have not appeared to show cross sensitivity to lidocaine. Lidocaine is also contraindicated in patients with a history of sensitivity to amide type local anesthetics. Xylocaine® 2% jelly also contains methylparaben, propylparaben and hydroxypropylmethylcellulose, as well as lidocaine; and, therefor, Xylocaine® is contraindicated for patients with known sensitivities to any of these compounds. See Astra Pharmaceuticals, product description 021838R11, June 1986; in Physician's Desk Reference, 45th Edition (1991), at p. 628.

As a result of adding the anesthetic to the $PGE_2$, it has been discovered by the inventor that the effect of the $PGE_2$ treatment is generally less pronounced. Thus, in a lidocaine-containing formulation, the dosage of $PGE_2$ must be increased over that in a non-lidocaine-containing formulation, and more preferably, the $PGE_2$ dosage is preferably doubled in a lidocaine-containing formulation in order to obtain the same effect on impotence.

More or less lubricant may be desired depending upon the delivery dose and concentration of the anesthetic jelly. In general, the total volume of the impotence treating unit does should be no more than 5 cc, and preferably from about 1 cc to no more than about 2 cc due to the inherent capacity of the urethra. Doses of excessive volume can result in painful administration, and also in retrograde migration of the excess formulation into the prostatic urethra or bladder.

Preferably, the total amount of $PGE_2$ contained in a unit dose will be within the range of from about 0.2 mg to about 5.0 mg. Due to differing etiology of erectile dysfunction, and inherent variations across a population in terms of responsiveness to pharmaceutical agents, some routine experimentation may be desired to determine optimum dosages for a given patient or class of patients.

In general, however, doses within the range of from about 0.5 to about 5.0, and preferably from about 0.6 to about 3.6 mg $PGE_2$, have generally proven sufficient in patients in which a response is likely to occur. Although it is not possible to predict with precision what types of patient populations will likely respond to the treatments disclosed herein, certain classes of patients are anticipated to be treatable depending upon the etiology of the condition. For example, patients in whom erectile dysfunction is associated with vascular abnormalities such as atherosclerosis which prevents adequate blood inflow are not likely to respond. Patients in whom the dysfunction is a result of such conditions as diabetes, denervation, or psychological status are expected to be more likely to respond.

In the antidotal or priapism treating PGF formulation, the PGF will generally be present in an amount within the range of from about 5 to about 50 μg per 1 cc does of formulation, preferably within the range of from about 8 to 20 μg/cc and more preferably about 12 μg/cc. As with the $PGE_2$ formulation, optimum dosage for a given patient can be determined through routine experimentation.

It has now been discovered that the burning and aching sensation can be eliminated without the use of an anaesthetic agent and the commenserate increase in $PGE_2$ to obtain the same effect. As described above, $PGF_{2\alpha}$ reverses the effect of $PGE_2$, i.e. terminates an erection. It has now been found that mixing small amounts of $PGF_{2\alpha}$ with $PGE_2$ eliminates the burning or aching experienced by some individuals when $PGE_2$ is used alone. It has further been discovered that, unlike the addition of an anaesthetic to $PGE_2$, adding $PGF_{2\alpha}$ does not reduce the beneficial effects of $PGE_2$ and additional amounts of $PGE_2$ are not required to obtain the same beneficial effects.

A suitable $PGE_2$ composition to eliminate the undersirable burning and aching sensation without noticably reducing the impotence treatment effect of the $PGE_2$ includes from about 0.5 μg to about 5.0 μg of $PGF_{2\alpha}$ Below about 0.5 μg the burning and aching may persist and above about 5 μg and erection may occur more slowly and may not be adequate for intercourse. A preferred composition includes about 1.0 μg of $PGF_{2\alpha}$ for each milligram of $PGE_2$.

Any of several different delivery systems may be utilized in accordance with the method of the present invention. For example, if a fluid or cream or gel system is used, the carrier can be absorbed directly, or allowed to be expelled following sufficient dwell time which may be controlled by occluding the distal end of the urethra.

Alternatively, more solid delivery vehicles may be used such as an ovoid or rod-shaped suppository. Suppositories can be formulated from any of a variety of materials which exhibit sufficient physical integrity to permit transurethral insertion and which will then permit delivery of the medication. Once installed, the structural component of the suppository may break down under the influence of body heat. Alternatively, materials can be used which will dissolve in an aqueous environment at a pH within the range of that typical of the urethra. One suitable composition is a mixture of glycerides of fatty acids such as that used with the Prostin E2® product.

The above noted burning sensation is also experienced when using $PGE_1$. It has been found that addition of $PGF_{2\alpha}$ has substantially the same effect when added to $PGE_1$ in a percentage to total dosage equivalent to that used with $PGE_2$. In adding $PGF_{2\alpha}$ to $PGE_1$ it should be recognized that more $PGE_1$ than $PGE_2$ is required to obtain a suitable erection for intercourse and, as a result, a higher dosage of $PGF_{2\alpha}$ may be required to get the same pain relief.

As a further alternative, a variety of drug delivery vehicles may be used which neither dissolve nor break down in the envirornent of the urethra. Relatively rigid rod-shaped delivery vehicles may be fashioned from materials having a microporous structure for the time release of entrapped pharmaceutical.

Such vehicles can be transurethrally inserted for a predetermined period of time and then removed following delivery of an efficacious amount of drug. Although the convenience of a self dissipating carrier is lost, the removable time release delivery structure may have the added advantage of providing some range of flexibility in the total delivered dose. Thus, the patient, by leaving the implant in place for relatively shorter or longer periods of time, can optimize the dose within a preset maximum range.

Particular embodiments of the present invention will be described in the Examples which follow.

EXAMPLE I

Preparation of Intraurethral $PGE_2$ Cream

A batch of $PGE_2$ cream was prepared by mixing a 40 mg $PGE_2$ suppository (obtained as the "Prostin $E_2$" suppository from the Upjohn Company) with 10 cc of 2% Xylocaine jelly and 50 cc of K-Y surgical lubrication jelly (hydroxyethyl-ellulose, obtained from Johnson & Johnson). Mixing was accomplished by stirring until the mixture appeared homogenous upon visual inspection. The result was a $PGE_2$ cream having approximately 1.3 mg of $PGE_2$ per 2 cc of cream.

EXAMPLE II

Preparation of Intraurethral $PGE_2$ Gel

The homogenecity of a bath of $PGE_2$ is ensured by inclusion of a methylene blue marker. One 20 mg $PGE_2$ suppository ("Prostin $E_2$" from the Uphohn Company) is sliced into thin slices and allowed to soften at room temperature for 15 minutes. A small drop of 1% methylene blue solution (American quinine, Shirley, N.Y.) is placed onto each slice to serve as a marker for homogenicity. The softened slices are thereafter geometrically mixed with the contents of a 56.7 gram tube of K-Y jelly to yield a homogenous mixture, as evidenced by blue color uniformity. The theoretical content of the final product is approximately 0.68 milligrams of $PGE_2$ per 2 cc of gel.

EXAMPLE III

Preparation of Lipid Based Intraurethral $PGE_2$ Cream

A batch of $PGE_2$ cream in cocoa butter is prepared by placing one 20 mg. $PGE_2$ suppository (Prostin $E_2$ by the Upjohn Company) into a porcelain evaporating dish and is melted in a 37° C. water bath. Shredded cocoa butter is added to the melted suppository with stirring to bring the total mass to approximately 20 grams. As the melting continues, the temperature of the mixture is kept at or below about 33° C. Higher temperatures are to be avoided, as they have been reported to cause the crystalline form of the cocoa butter to change, resulting in aberrations in bioavailability. Transformations in the crystalline form of the cocoa butter are visually observed as a change from opalescent to transparent. After complete melting, the mixture is stirred thoroughly and poured into suppository molds. The material is thereafter allowed to cool at room temperature for about 15 minutes, and thereafter is placed in the refrigerator to facilitate further solidification. The suppositories may thereafter be removed from the mold, individually packaged and placed in refrigerated storage under anhydrous conditions.

EXAMPLE IV
Administration of Intraurethral $PGE_2$ Cream

Two cc of the $PGE_2$ cream from Example I was instilled into the urethral meatus of each of 10 impotent male patients between the ages of 50 and 70, using a syringe. The cream was massaged down the urethra, and then the distal end of the urethra was occluded for 5 minutes by manual pressure.

EXAMPLE V
Efficacy of $PGE_2$ Cream in Treating Human Erectile Dysfunction

The effect of administration of $PGE_2$ cream, prepared and administered in accordance with the procedures of Examples I and IV, was observed. After 15 to 30 minutes, treatment response was rated as no penile tumescence, partial tumescence or full tumescence.

As a result, two of the ten men treated had no response, six had partial tumescence, and two had full tumescence. Thus, 80% of the men treated showed at least partial penile tumescence in response to the intraurethral $PGE_2$ cream.

EXAMPLE VI
Efficacy of Lower Concentrations of $PGE_2$ Cream in Treating Human Erectile Dysfunction $PGE_2$ cream was prepared and administered in accordance with the procedures of Examples I and IV, except that a 20 mg $PGE_2$ suppository was used instead of a 40 mg suppository. This cream contained approximately 0.7 mg of $PGE_2$ per 2 cc of cream. Two cc of cream was used to treat each of ten impotent men between the ages of 50 and 70. After 15 to 30 minutes, treatment response was rated as no penile tumescence, partial tumescence, or full tumescence.

As a result, four of the ten men treated had no response, two had partial tumescence, and four had full tumescence. Thus, even using lower concentrations of $PGE_2$, 60% of the men treated showed at least partial penile tumescence in response to the intraurethral $PGE_2$ cream.

EXAMPLE VII
Use of $PGF_{2\alpha}$ to Counteract Effects of Administration of $PGE_2$ Priapism resulting from the $PGE_2$ treatment in accordance with the present invention has been determined to be reversible or treatable through the application of an effective antidotal amount of a 15 methyl substituted prostaglandin $F_{2\alpha}$ containing formulation. In addition, it is anticipated that priapism of a variety of other etiology will be similarly treatable.

An antidotal formulation is prepared by mixing approximately 250 micrograms of prostaglandin $F_{2\alpha}$ obtained as Hemabate, marketed by Upjohn, in approximately 20 cc of K-Y jelly. Mixing is accomplished manually until visual observation reveals a homogenous composition. A dose of approximately 1 cc of the foregoing formulation is instilled in accordance with Example IV, to reverse the results of the $PGE_2$ treatment in accordance with the present invention.

EXAMPLE VIII
Use of a $PGE_2/PGF_{2\alpha}$ Combination to Treat Impotence

Freeze dried $PGE_2$ was obtained from Chinoin Pharmaceutical and Chemical Works Co. Ltd., Budapest, Hungary. Three different solutions were prepared with $PGE_2$ concentration being 0.5, 0.75 or 1.0 mg/0.1 cc of physiological saline. To the 0.1 cc of solution, $PGF_{2\alpha}$ in the amount of 1.0 $\mu$g/1.0 mg $PGE_2$ was added and the solution was instilled into the urethra of a normally impotent male at a distance of at least about 1 cc from the external opening of the urethra. An erection suitable for sexual intercourse occured within about 3 to 5 minutes after placement of the solution and the erection lasted about 1 hour. No burning or aching was experienced and the erectile effect and sustainability of the erection appeared to the treated individual to be undistinguishable from that of a control comprising a similarly prepared solution without the addition of the $PGF_{2\alpha}$. The only noticable difference was a burning sensation along the urethra encountered only with the control solution.

Although this invention has been described in terms of certain preferred embodiments, other embodiments that are apparent to those of ordinary skill in the art are also within the scope of the invention. In particular, analogs or derivatives of $PGE_2$ and $PGF_{2\alpha}$ which do not affect the basic functionality of those molecules as described herein are also considered within the scope of the present invention. Accordingly, the scope of the invention is intended to be defined only by reference to the appended claims.

I claim:

1. A method of treating erectile dysfunction in a male patient comprising the step of administering to the urethra of said patient a unit dose of a mixture of
   a) $PGF_{2\alpha}$, a physiologically acceptable salt thereof, or a physiologically acceptable ester thereof, or a mixture thereof, and
   b) an erectile inducing prostaglandin, said erectile inducing prostaglandin selected from the group consisting of $PGE_1$, $PGE_2$, a physiologically acceptable salt thereof, a physiologically acceptable ester thereof, and mixtures thereof,
   the mixture of a) and b) above carried in a readily dispersable pharmaceutically acceptable delivery medium.

2. The method of claim 1 wherein the unit dose contains from about 0.5 $\mu$g to about 5.0 $\mu$g of $PGF_{2\alpha}$.

3. The method of claim 1 wherein the unit dose contains about 1 $\mu$g of $PGF_{2\alpha}$ for each milligram of erectile inducing prostaglandin.

4. The method of claim 1 wherein the unit dose contains from about 0.5 $\mu$g to about 5.0 $\mu$g of $PGF_{2\alpha}$ and about 1 $\mu$g of $PGF_{2\alpha}$ for each milligram of $PGE_2$.

5. A composition for treating erectile dysfunction in a male patient comprising a mixture of
   a) $PGF_{2\alpha}$, a physiologically acceptable salt thereof, or a physiologically acceptable ester thereof, or a mixture thereof and
   b) an erectile inducing prostaglandin, said erectile inducing prostaglandin selected from the group consisting of $PGE_1$, $PGE_2$, a physiologically acceptable salt thereof, a physiologically acceptable ester thereof, and a mixture thereof,
   the mixture of a) and b) above carried in a readily dispersable pharmaceutically acceptable delivery medium.

6. The composition of claim 5 wherein a unit dose thereof contains from about 0.5 $\mu$g to about 5.0 $\mu$g of $PGF_{2\alpha}$.

7. The composition of claim 5 wherein a unit dose thereof contains about 1.0 $\mu$g of $PGF_{2\alpha}$ for each milligram of erectile inducing prostaglandin.

8. The composition of claim 6 wherein a unit dose comprises 0.1 cc to 0.5 cc of a solution containing from about 0.2 to about 5.0 mg of erectile inducing prostaglandin.

9. The composition of claim 8 wherein the unit dose comprises 0.1 cc to 0.5 cc of a solution containing from about 0.5 to about 3.6 mg of erectile inducing prostaglandin.

10. The composition of claim 8 wherein the unit dose comprises 0.1 cc of solution containing from about 0.5 to about 1.0 mg of $PGE_2$.

11. The composition of claim 9 wherein the unit dose thereof contains about 1.0 µg of $PGF_{2\alpha}$ for each milligram of erectile inducing prostaglandin.

12. The composition of claim 11 wherein the unit dose thereof contains about 1.0 µg of $PGF_{2\alpha}$ for each milligram of $PGE_2$.

* * * * *